United States Patent [19]

Chinn

[11] 4,349,474
[45] Sep. 14, 1982

[54] 2-CYANOSTEROIDS

[75] Inventor: Leland J. Chinn, Morton Grove, Ill.

[73] Assignee: G. D. Searle & Co., Skokie, Ill.

[21] Appl. No.: 287,341

[22] Filed: Jul. 27, 1981

[51] Int. Cl.³ .............................................. C07J 71/00
[52] U.S. Cl. ......................... 260/239.55 C; 260/397.3
[58] Field of Search .................... 260/239.55 C, 397.4, 260/397.3

[56] References Cited

U.S. PATENT DOCUMENTS 3,966,926  6/1976  Potte .................................. 424/240
4,029,776  6/1977  Cafruny et al. ..................... 424/240

*Primary Examiner*—Elbert L. Roberts
*Attorney, Agent, or Firm*—James G. Passe

[57] ABSTRACT

The invention relates to novel 2-cyanosteroids of Formula I which are useful for the induction of menses and the termination of pregnancy.

9 Claims, No Drawings

2-CYANOSTEROIDS

BACKGROUND OF THE INVENTION

The present invention relates to certain novel organic compounds. In particular the invention relates to certain 2-cyanosteroids useful for the induction of menses and the termination of pregnancy in mammals.

Compounds which show activity for induction of menses and termination of pregnancy are well known. Estrogens have been used widely for induction of menses in the menopausal female see e.g. U.S. Pat. No. 4,154,820. Progesterone and its derivatives have been shown to be useful for primary and secondary amenorrhea as described by Wiechert in U.S. Pat. No. 3,812,166.

PRIOR ART

Various steroids are known in the art for control of menses and induction of pregnancy as indicated above. In addition, U.S. Pat. No. 3,246,255 describes a 2-cyanosteroid that shows activity as pituitary inhibitors, electrolyte modifying agents, and hypotensive coronary dilators. U.S. Pat. No. 1,160,027 describes certain 2-cyano-4,5-epoxy steroids useful as interceptive agents.

SUMMARY OF THE INVENTION

The invention particularly provides a compound according to Formula I:
wherein $R_1$ is:
(a) hydrogen; or
(b) methyl;
wherein $R_2$, $R_3$, and $R_4$ are:
(a) hydrogen; or
(b) methyl; with a double bond at either the 4,5 or the 5,6 position; $R_2$, $R_3$, and $R_4$ each being the same or different.
wherein $R_5$ is:
(a) methyl; or
(b) the terminus of a double bond at C—13 and 14;
wherein $R_6$ is:
(a) hydrogen; or
(b) methyl;
wherein $R_7$ is:
(a) methyl; or

(b)

wherein $R_8$ is:
(a) —OCH$_2$CH$_2$O—;
(b) —SCH$_2$CH$_2$S—; or
(c) =N—O—R$_9$;
wherein $R_9$ is:
(a) hydrogen; or
(b) alkyl of one to six carbon atoms inclusive.

Examples of alkyl of from one to six carbon atoms, inclusive, are methyl, ethyl, propyl, butyl, pentyl and hexyl and the isomeric forms thereof.

Successful implantation and the maintenance of the initial stages of pregnancy in humans are dependent upon the availability of adequate amounts of ovarian progesterone. An important step in the biosynthetic pathway for progesterone is the conversion of pregnenolone to progesterone. This reaction is catalyzed by the $\Delta^5,3\beta$-hydroxysteroid dehydrogenase/$\Delta^{5-4}$, 3 ketoisomerase ($\Delta^5,3\Delta$-HSD) enzyme system. Several known inhibitors of this enzyme system have already been shown to selectively or predominantly inhibit either gonadal/placental production of progesterone (see Creange et al., Fertility and Sterility 30: pps 86-90, 1978) or the adrenal production of progesterone (see Potts et al., Steroids 32: pps 267-276, 1978). An in vitro technique for measuring the amount of progesterone produced by luteal microsomes incubated at 37° C. with pregnenolone as substrate and NAD as cofactor has been developed. The progesterone produced can be measured spectrophotometrically in the ultraviolet range at 240 nm. Drugs which inhibit biosynthesis of progesterone would be useful as contraceptive and contragestational agents.

A. Incubation

Luteal tissue is collected from immature pseudopregnant rats on day three or four and homogenized at 8 milligrams per milliliter in 0.25 M sucrose in Kreb's Ringer bicarbonate solution without calcium (pH 7.4) and centrifuged at 750× g for ten minutes to remove nuclei and cell debris. The supernatant is then centrifuged at 7,000× g for twelve minutes to remove the mitochondria, leaving only the microsome-cytosol in the supernatant. Pregnenolone is used as substrate in a concentration of 157.2 μm and 4.04 micromoles (6 milligrams/0.5 ml) NAD is used as cofactor. The order of addition of components of the incubate is 0.1 ml pregnenolone solution (100 micrograms/0.1 ml ethanol), 0.5 ml buffer, 0.02 ml ethanol or the inhibitor in 0.02 ml ethanol (when tested), 1 ml microsome-cytosol and 0.5 ml NAD solution thus making up a total volume of 2.12 ml. The reaction is initiated by the addition of the cofactor. The incubation is carried out for one hour at 37° C. At the end of one hour incubation samples are immersed in a Dry Ice ethanol bath to stop the reaction. Samples are stored at minus 20° C. until extraction for progesterone with petroleum ether.

B. Extraction

Incubates are thawed in a warm water bath at 50° C. and extracted twice with petroleum ether. The extract is dried under an air manifold and reconstituted in 2 ml of absolute ethanol. The progesterone concentration of the reconstitute is determined in a standard size quartz cuvette in a Gilford 240 spectrophotometer at 240 nm (uv). A standard progesterone curve is prepared using progesterone diluted in absolute ethanol in doses of 1,2,4,8,12,16,20,40,60,80 and 100 micrograms/0.1 ml. These doses were added to 2.0 ml of deionized distilled water and extracted along with the samples from each incubation.

By virtue of the above described activity the compounds of Formula I are useful in inducing menses and for the termination of pregnancy. A physician of ordinary skill could readily determine a subject who is in need of such treatment. Regardless of the route of administration selected, compounds of the present invention can be formulated into pharmaceutically acceptable dosage forms by conventional methods known to the pharmaceutical art.

The compounds can be administered in such oral unit dosage forms as tablets, capsules, pills, powders or granules. They also may be administered rectally, vaginally in such forms as suppositories or bougies. They also may be introduced in the form of eyedrops, interparentally, subcutaneously or entramuscularly, using forms known to the pharmaceutical art. In general, the preferred form of administration is oral.

An effective but non-toxic quantity of the compound is employed in treatment. The dosage regimen of the compounds of this invention is selected in accordance with a variety of factors including the type, age, weight and medical condition of the mammal, the route of administration and the particular compound employed. An ordinary skilled physician or veterinarian will readily determine and prescribe the effective amount of the compound of the instant invention.

Dosages of the compound of the invention are ordinarily in the area of 1 milligram per kilogram up to at most 20 milligrams per kilogram orally. When other forms of administration are employed equivalent doses are administered.

Starting materials are shown on FIGS. 2, 3, and 4 on Chart A. The 3-ketosteroid, Formula II, is dissolved in a cold aprotic solvent such as toluene and is treated with ethyl formate and sodium hydride and allowed to react at ambient temperatures. Upon completion of the reaction the mixture is quenched with water and purified by extractions and distillations or chromatography producing the 2-hydroxymethylene (or formyl) derivatives of Formula III. Compounds of Formula III are then reacted with hydroxylamine in an alcoholic solvent which affords cyclization to the corresponding isaxazole compounds (Formula IV of Chart A). Reaction with an alkaline metal alkoxide converts the isoxazoles to ring opened 2-cyano-3-cytosteroids of Formula V.

Reactions for other functional groups of the steroid molecules can be affected in addition to or in concert with the reactions described herein producing new embodiments of the basic structures described.

The invention will appear more fully from the Examples which follow. These Examples are given by way of illustration only and are not to be construed as limiting the invention either in spirit or in scope as many modifications both in materials and methods will be apparent from this disclosure to those skilled in the art. In these examples temperatures are given in degrees centigrade (°C.) and quantities of materials in grams and milliliters unless otherwise noted.

DESCRIPTION OF THE PREFERRED EMBODIMENTS

Example 1

6α,17,17-trimethyl-3-oxo-18-norandrosta-4,13-diene-2-carbonitrile.

To a solution of 1.3 g of an appropriate compound of Formula II in 50 ml of dry toluene stirred in an ice bath is added in succession 1.7 ml of ethyl formate and a sample of sodium hydride, which is prepared by washing free of oil 1.1 g of a 50 percent dispersion of sodium hydride in mineral oil with hexane. The reaction mixture is stirred in an atmosphere of nitrogen for two hours at 4° C. and then for 25 hours at ambient temperature. The reaction mixture is again cooled in an ice bath and carefully diluted with water. After acidification with 6 N hydrochloric acid the mixture is extracted with ether. The ether extract is washed successively with water and saturated with sodium chloride, dried over anhydrous sodium sulfate and distilled to dryness under reduced pressure to produce the 2-hydroxymethylene derivative. 1.2 g of the derivative is placed into solution with 480 mg of hydroxylamine hydrochloride and 516 mg of sodium acetate in 40 ml of 95 percent ethanol and is heated under reflux for five minutes and then allowed to stand at ambient temperature for 45 minutes. The reaction mixture is diluted with water and acidified with 6 N hydrochloric acid. The mixture is extracted with ether. The ether extract is washed successively with water and saturated sodium chloride, dried over anhydrous sodium sulfate, and evaporated to dryness to afford an isoxazole. To a solution of 1.0 g of the isoxazole in 10 ml of methanol is added 600 mg of sodium methoxide. The resultant mixture is stirred at ambient temperature for one and a half hours. Then it is diluted with water and acidified with 6 N hydrochloric acid. The product is separated and crystallized from an ether-hexane solvent system to afford the title compound having a melting point of 163°–165° C.

EXAMPLE 2

4,4,17,17-tetramethyl-3-oxo-18-norandrosta-5,13-diene-2α-carbonitrile

Using the procedures described in Example 1 and using appropriate starting materials the title compound is prepared.

EXAMPLE 3

17,17-dimethyl-3-oxogona-4,13-diene-2α-carbonitrile

To a solution of 1.5 g of 17,17-dimethyl-gona-4,13-dien-3-one and 80 ml of dry toluene cooled in an ice bath is added in succession 2.5 ml of ethyl formate and 1.5 g of a 50 percent dispersion of sodium hydride. The reaction mixture is stirred in an atmosphere of nitrogen for two hours at 4° C. and then at ambient temperature for 20 hours. The reaction mixture is again cooled to 4° C. and then diluted with water. The organic phase is separated and extracted successively with a 5 percent sodium hydroxide solution and water. The combined aqueous and alkaline solutions are acidified with hydrochloric acid. The resultant acidified mixture is extracted with ether. The ether extract is washed with water, dried over anhydrous sodium sulfate and distilled to dryness under reduced pressure to afford an oil. To the solution of 1.5 g of the oil in 30 ml of 95 percent ethanol are added 350 mg of hydroxylamine hydrochloride and 420 mg of sodium acetate. The reaction mixture is stirred at ambient temperature for 16 hours and then heated under reflux for two hours. The cooled mixture is diluted with water and extracted with ether. The ether extract is washed with water, dried over anhydrous sodium sulfate and evaporated to dryness. The residue is chromatographed. The solid obtained is recrystallized from methanol to afford the isoxazole (Formula 4) having a melting point of 115°–117° C. To a solution of 442 mg of the isoxazole and 35 ml of dry toluene is added a solution of 900 mg of sodium methoxide in 20 ml of methanol. The reaction mixture is stirred at ambient temperature for 18 hours in an atmosphere of nitrogen. Then it is diluted with 500 ml of water and acidified with 6 N hydrochloric acid. The organic phase is separated, washed with water, dried over anhydrous sodium sulfate and evaporated to dryness. The residue is crystallized from ether to afford the title compound having a melting point of 163°–165° C.

EXAMPLE 4

17,17-dimethyl-3-oxo-18-norandrosta-4,13-diene-2α-carbonitrile

A solution of 2.0 g of 17,17-dimethyl-18-norandrosta-4,13-dien-3-one and 50 ml of dry toluene is cooled in an ice bath, 4° C. and to the solution is added in succession 1.7 ml of ethyl formate and a sample of sodium hydride which was prepared by washing 1.1 g of a 50 percent dispersion of sodium hydride in mineral oil with hexane. The reaction mixture is stirred in the ice bath in an atmosphere of nitrogen for three hours and then at ambient temperature for 23 hours. The reaction mixture is again cooled in the ice bath. It is then carefully diluted with water. The aqueous phase is separated and acidified with 6 N hydrochloric acid. The acidified mixture is extracted with methylene chloride. The methylene chloride extract is evaporated to dryness to afford the hydroxymethylene compound (Formula III). A solution of 1.5 g of the hydroxymethylene compound, 480 mg of hydroxylamine hydrochloride and 560 mg of sodium acetate, 40 ml of 95 percent ethanol is stirred and heated under reflux for one hour. The cooled reaction mixture is diluted with water and then extracted with ether. The ether extract is washed with water, dried over anhydrous sodium sulfate and evaporated to dryness. The residue is chromatographed on silica gel to afford a viscous oil. A solution of 770 mg of the viscous oil, 500 mg of sodium methoxide and 15 ml of methanol is stirred at ambient temperature for 2 hours. Then it is diluted with 200 ml of water. The mixture is acidified with 6 N hydrochloric acid. The resultant precipitate is collected, washed with water and dried. It is crystalized from ether to afford the title compound having a melting point of 165°–167° C.

EXAMPLE 5

20-oximino-4,4-dimethyl-3-oxopregn-5-ene-2α-carbonitrile

To a solution of 28 g (0.067 M) of 2-hydroxymethylene-4,4-dimethyl-5-pregnene-3,20-dione 20-monoethylene glycol ketal in 680 ml of ethanol and 14 ml of water is added a slurry of 5.2 g (0.748 m) of hydroxylamine hydrochloride and 5.48 g (0.0665 m) of sodium acetate. After the mixture is refluxed for half an hour an additional 2.5 g of (0.36 M) hydroxylamine and 2.5 g (0.30 M) of sodium acetate is added and the mixture refluxed for 45 minutes. Most of the ethanol is removed by concentration on vacuo. Water is added and the mixture is extracted with ether. The ether extracts are washed with water, dried over sodium sulfate, concentrated and the residue is crystallized from methanol to give 1.1 gram of 20-oximino-4,4α-dimethyl-3-oxo pregn-5-eno[2,3-d] isoxazole.

To a solution of 2 g (0.0053 M) of 4,4-dimethyl-20-oximino-5-pregeno[2,3-d]isoxazole in 36 ml of methanol and 16 ml of tetrahydrofuran is added 0.8 g (0.16 M) of sodium methoxide. After stirring for two hours at room temperature the solvent is evaporated off under nitrogen atmosphere. The residue is cooled in an ice bath, acidified with 10 percent hydrochloric acid solution and then stirred for 15 minutes. The acidified mixture is extracted with ethyl acetate. The ethyl acetate extract is washed with water, dried over sodium sulfate and concentrated in vacuo. The residue is crystallized from a methylene chloride-hexane solvent system to give the title compound having a melting point of 190°–192° C.

EXAMPLE 6

20,20-(1,2-ethylenebisoxy)-4,4-dimethyl-3-oxopregn-5-ene-2α-carbonitrile

To a solution of 0.55 g (0.00134 M) of 4,4-methyl-3,20-dioxo-5-pregneno[2,3-d]isoxazole-20-monoethylene ketal in 7 ml of methanol and 5 ml of tetrahydrofuran is added 0.22 g (0.0041 M) of sodium methoxide. After stirring for two hours at room temperature the solvents are evaporated under nitrogen atmosphere. The residue is diluted with water, cooled in an ice bath and carefully acidified with cold 10 percent hydrochloric acid. The acidified mixture is extracted with ether and the ether extracts are washed with water, dried over anhydrous sodium sulfate and concentrated in vacuo. The residue is crystallized from a methylene chloride/hexane solvent system to give the title compound having a melting point of 176°–178° C.

CHART A

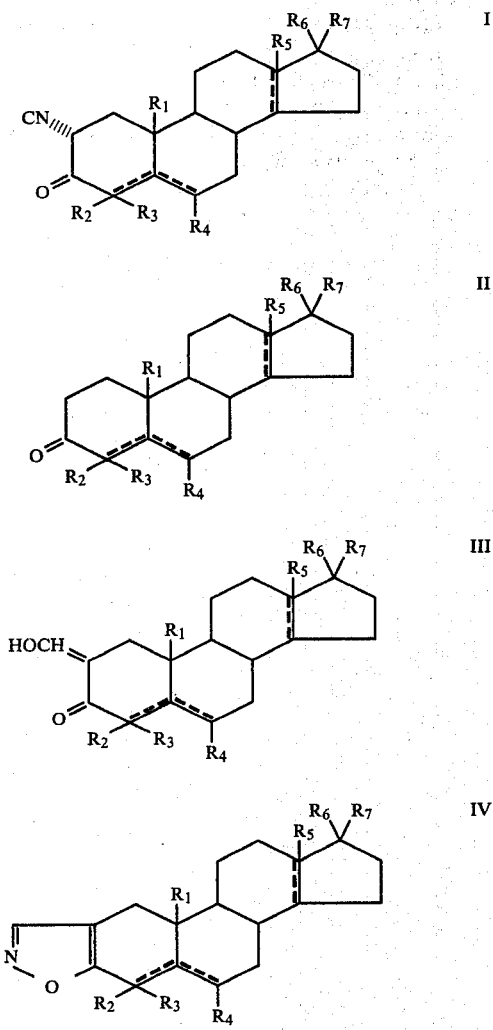

-continued
CHART A

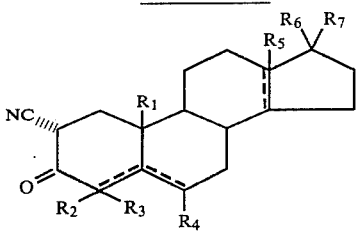

I claim:
1. A compound according to formula I:

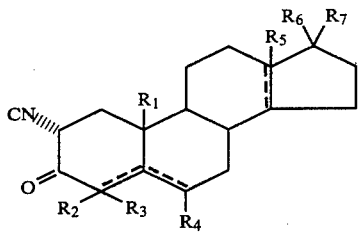

wherein $R_1$ is:
  (a) hydrogen; or
  (b) methyl;
wherein $R_2$, $R_3$ and $R_4$ is:
  (a) hydrogen; or
  (b) methyl; with a double bond at either the 4,5 or 5,6-position; $R_2$, $R_3$ and $R_4$ each being the same or different.
wherein $R_5$ is:
  (a) methyl; or
  (b) the terminus of a double bond at C—13 and 14;
wherein $R_6$ is:
  (a) hydrogen; or
  (b) methyl;
wherein $R_7$ is:
  (a) methyl; or

 (b)

wherein $R_8$ is:
  (a) —OCH$_2$CH$_2$O—;
  (b) —SCH$_2$CH$_2$S—; or
  (c) =N—O—R$_9$
wherein $R_9$ is:
  (a) hydrogen; or
  (b) alkyl of from one to six carbon atoms, inclusive.

2. A compound according to claim 1 wherein the bond between carbons 4 and 5 is unsaturated.

3. 17,17-dimethyl-3-oxo-gona-4,13-diene-2α-carbonitrile, a compound according to claim 2.

4. 17,17-dimethyl-3-oxo-18-norandrosta-4-13-diene-2α-carbonitrile, a compound according to claim 2.

5. 6α,17,17-trimethyl-3-oxo-18-norandrosta-4,13-diene-2-carbonitrile, a compound according to claim 2.

6. A compound according to claim 1 wherein the bond between carbons 5 and 6 is unsaturated.

7. 4,4,17,17-tetramethyl-3-oxo-18-norandrosta-5,13-diene-2α-carbonitrile, a compound according to claim 6.

8. 20-oximino-4,4-dimethyl-3-oxopregn-5-ene-2α-carbonitrile, a compound according to claim 6.

9. 20,20-(1,2-ethylenebisoxy)4,4-dimethyl-3-oxopregn-5-ene-2α-carbonitrile.

* * * * *